(12) United States Patent
David

(10) Patent No.: US 8,547,538 B2
(45) Date of Patent: Oct. 1, 2013

(54) CONSTRUCTION OF REFERENCE SPECTRA WITH VARIATIONS IN ENVIRONMENTAL EFFECTS

(75) Inventor: Jeffrey Drue David, San Jose, CA (US)

(73) Assignee: Applied Materials, Inc., Santa Clara, CA (US)

(*) Notice: Subject to any disclaimer, the term of this patent is extended or adjusted under 35 U.S.C. 154(b) by 223 days.

(21) Appl. No.: 13/091,965

(22) Filed: Apr. 21, 2011

(65) Prior Publication Data

US 2012/0268738 A1 Oct. 25, 2012

(51) Int. Cl.
*G01N 21/00* (2006.01)

(52) U.S. Cl.
USPC .......................................................... 356/72

(58) Field of Classification Search
USPC .......................................................... 356/326
See application file for complete search history.

(56) References Cited

U.S. PATENT DOCUMENTS

| | | |
|---|---|---|
| 6,361,646 B1 | 3/2002 | Bibby et al. |
| 6,707,540 B1 | 3/2004 | Lehman |
| 2006/0166606 A1 | 7/2006 | Kobayashi et al. |
| 2007/0019205 A1 | 1/2007 | Namkoong |
| 2007/0224915 A1 | 9/2007 | David et al. |
| 2007/0251922 A1 | 11/2007 | Swedek et al. |
| 2009/0182520 A1* | 7/2009 | Luxembourg et al. ........... 702/81 |
| 2010/0015889 A1* | 1/2010 | Shimizu et al. .................... 451/5 |
| 2010/0103422 A1 | 4/2010 | David et al. |
| 2010/0105288 A1 | 4/2010 | David et al. |
| 2010/0114532 A1 | 5/2010 | David et al. |

FOREIGN PATENT DOCUMENTS

WO WO 00/57127 9/2000

OTHER PUBLICATIONS

Authorized Officer Y. J. Kim, International Search Report in International Application No. PCT/2012/034109, mailed Nov. 30, 2012, 9 pages.

* cited by examiner

*Primary Examiner* — Tarifur Chowdhury
*Assistant Examiner* — Abdullahi Nur
(74) *Attorney, Agent, or Firm* — Fish & Richardson P.C.

(57) ABSTRACT

A method of generating a library of reference spectra includes storing at least one reference spectrum, storing a plurality of different transmission curves, and for at least two transmission curves from the plurality of different transmission curves, calculating a modified reference spectrum from the reference spectrum and the transmission curve to generate a plurality of modified reference spectra. The transmission curves represent distortion to a spectrum introduced by variations in components in an optical path before a substrate surface.

20 Claims, 9 Drawing Sheets

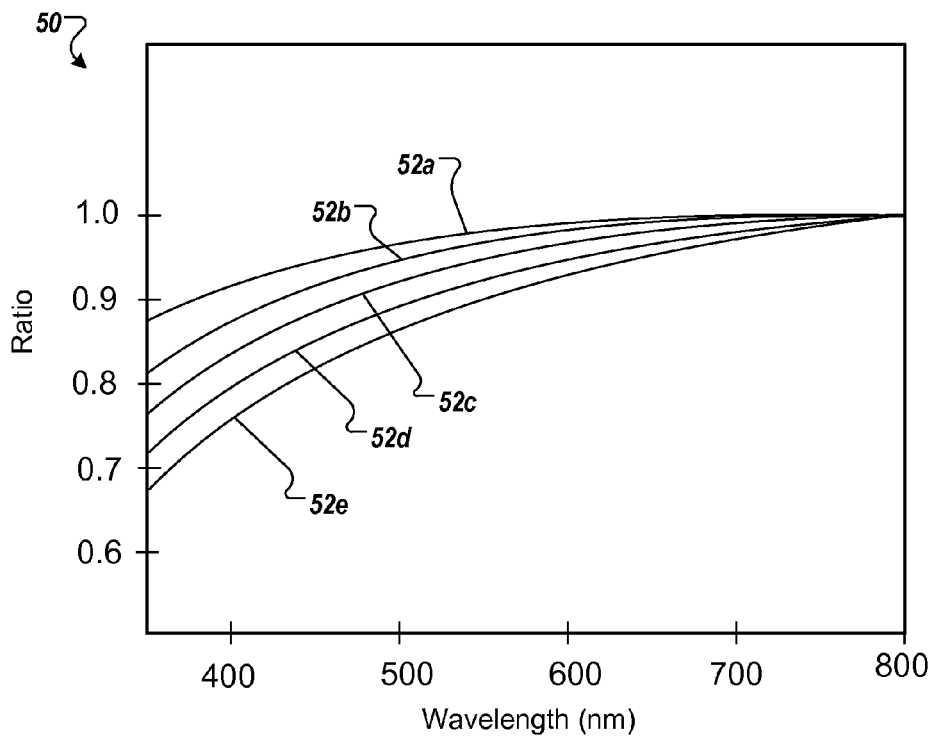
FIG. 1
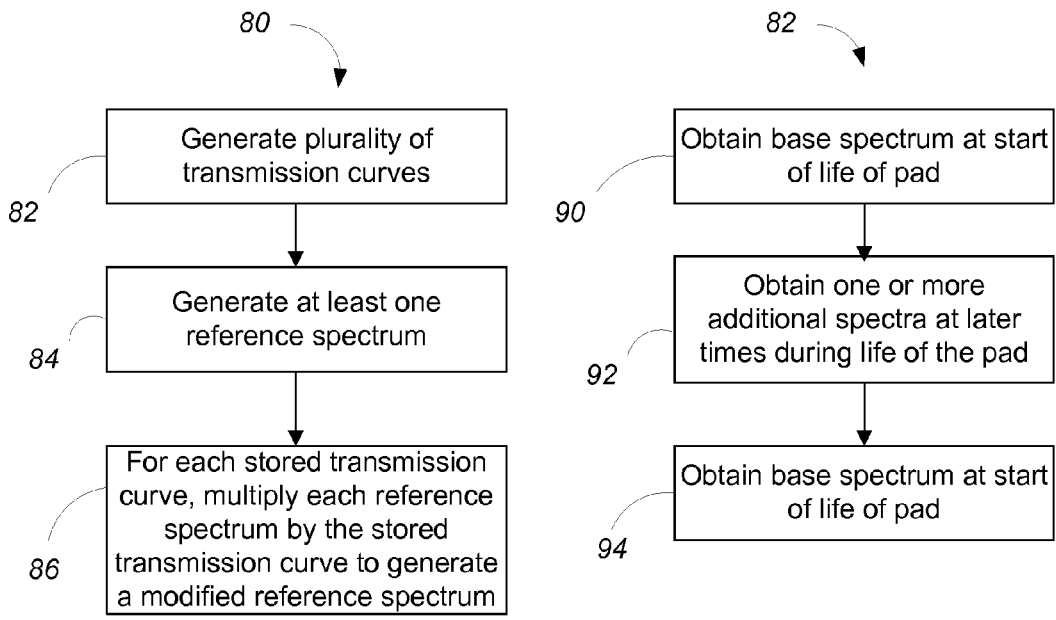
FIG. 5A
FIG. 5B

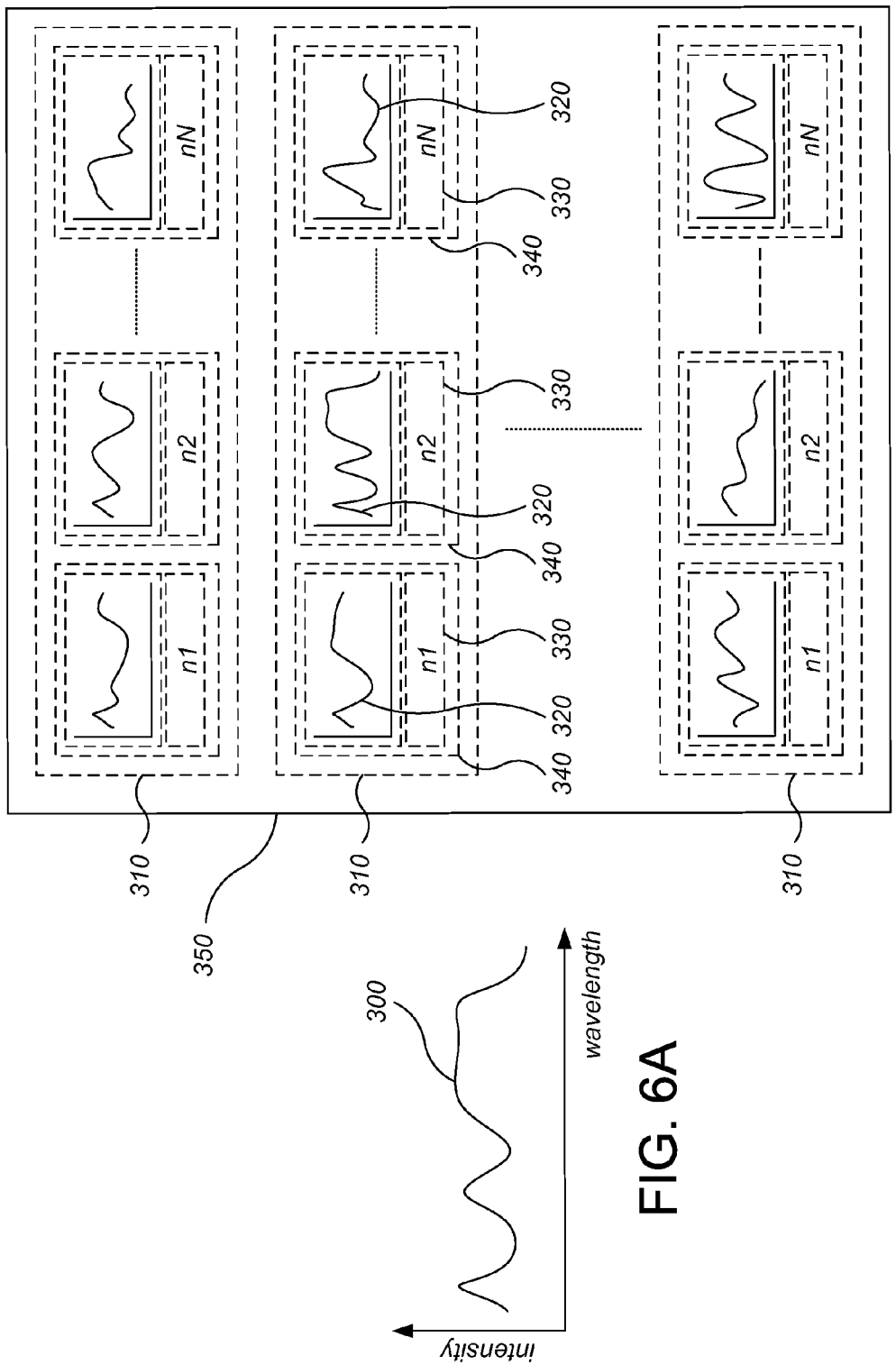

CONSTRUCTION OF REFERENCE SPECTRA WITH VARIATIONS IN ENVIRONMENTAL EFFECTS

TECHNICAL FIELD

The present disclosure relates to optical monitoring, e.g., during chemical mechanical polishing of substrates.

BACKGROUND

An integrated circuit is typically formed on a substrate by the sequential deposition of conductive, semiconductive, or insulative layers on a silicon wafer. One fabrication step involves depositing a filler layer over a non-planar surface and planarizing the filler layer. For certain applications, the filler layer is planarized until the top surface of a patterned layer is exposed. A conductive filler layer, for example, can be deposited on a patterned insulative layer to fill the trenches or holes in the insulative layer. After planarization, the portions of the conductive layer remaining between the raised pattern of the insulative layer form vias, plugs, and lines that provide conductive paths between thin film circuits on the substrate. For other applications, such as oxide polishing, the filler layer is planarized until a predetermined thickness is left over the non planar surface. In addition, planarization of the substrate surface is usually required for photolithography.

Chemical mechanical polishing (CMP) is one accepted method of planarization. This planarization method typically requires that the substrate be mounted on a carrier head. The exposed surface of the substrate is typically placed against a rotating polishing pad. The carrier head provides a controllable load on the substrate to push it against the polishing pad. A polishing liquid, such as a slurry with abrasive particles, is typically supplied to the surface of the polishing pad.

One problem in CMP is determining whether the polishing process is complete, i.e., whether a substrate layer has been planarized to a desired flatness or thickness, or when a desired amount of material has been removed. Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, it may not be possible to determine the polishing endpoint merely as a function of polishing time.

In some systems, a substrate is optically monitored in-situ during polishing, e.g., through a window in the polishing pad. However, existing optical monitoring techniques may not satisfy increasing demands of semiconductor device manufacturers.

SUMMARY

In some optical monitoring processes, a spectrum measured in-situ, e.g., during the polishing process, is compared to a library of reference spectra to find the best matching reference spectrum. One potential problem is that an optical property of one or more components in the optical path before the substrate surface. For example the transmission of the window in the polishing pad can change as the pad ages, and the optical property can be different from pad-to-pad. Since the optical monitoring system receives light passing through the window, this change results in distortion in the spectrum (e.g., as compared to what the optical monitoring system would measure for a "fresh" window). This distortion can reduce the accuracy of the endpoint detection system. In addition, where a best matching reference spectrum is selected from a library, the distortion increases the likelihood that the incorrect reference spectrum is selected as the best match (e.g., under the assumption that a correct reference spectrum would be selected for a "fresh" window). As another example, the spectral intensity of the bulb in the light source can change as the bulb ages, or can differ from bulb-to-bulb. One technique to address this problem is to build one or more libraries of reference spectra that incorporate the distortion caused by variation of components in the optical path before the substrate surface. For example, the library can include multiple reference spectra with different reference spectra incorporating different amounts of distortion.

In one aspect, a method of generating a library of reference spectra includes storing at least one reference spectrum, storing a plurality of different transmission curves, and for at least two transmission curves from the plurality of different transmission curves, calculating a modified reference spectrum from the reference spectrum and the transmission curve to generate a plurality of modified reference spectra. The transmission curves represent distortion to a spectrum introduced by variations in components in an optical path before a substrate surface.

Implementations can include one or more of the following features. The different transmission curves may represent variations in transmission of one or more windows, such as distortion to a spectrum at different ages of a window of a polishing pad or variations in transmission between different windows. The different transmission curves may represent distortion to a spectrum at different ages of a bulb from a light source. User input may be received identifying the at least two transmission curves from the plurality of different transmission curves. The plurality of different transmission curves may be generated. Generating the plurality of different transmission curves may include measuring a base spectrum from a test substrate using the in-situ optical monitoring system and measuring one or more additional spectra from the same test substrate or another test substrate of the same material using the in-situ optical monitoring system at different times, and calculating the transmission curves from the base spectrum and the one or more additional spectra. The different times may be different ages of a window of polishing pad in an optical path between the test substrate and a light source or detector of the in-situ optical monitoring system. The different times may be different ages of a bulb of a light source of the in-situ optical monitoring system. Calculating the transmission curves may include a division operation in which the additional spectrum is in the numerator and the base spectrum is in the denominator. A first dark spectrum at the same age of the window as the base spectrum and measuring a second dark spectrum at the same age of the window as the additional spectrum may be measured. Calculating the transmission curves may include calculating $T=(A-D_A)/(B-D_B)$, where A is the additional spectrum, $D_A$ is the second dark spectrum, B is the base spectrum, and $D_B$ is the first dark spectrum. The test substrate may be a bare silicon wafer. Generating the plurality of different transmission curves may include calculating the transmission curves from an optical model. Calculating the modified reference spectrum may include multiplying the reference spectrum by the transmission curve. The transmission curve may be stored as a ratio between 0 and 1 as a function of wavelength. The at least one reference spectrum may be generated, e.g., by measuring a test substrate during a polishing operation using the optical monitoring system, or by calculating the reference spectrum from an optical model.

In another aspect, a method of controlling polishing includes generating a library of reference spectra according to the prior method, polishing a substrate, measuring a sequence of spectra of light from the substrate during polishing, for each measured spectrum of the sequence of spectra, finding a best matching reference spectrum to generate a sequence of best matching reference spectra, and determining at least one of a polishing endpoint or an adjustment for a polishing rate based on the sequence of best matching reference spectra. In another aspect.

In another aspect, a computer program product, tangibly embodied in a machine readable storage device, includes instructions to carry out the method.

Implementations may optionally include one or more of the following advantages. A library of reference spectra that spans the likely range of influence of the window on the light can be calculated, either from an optical model or from empirically collected spectra. The resulting library of reference spectra enable the matching algorithm to remain reliable when there is variation in transmission of the window. Thus, reliability of the endpoint system to detect a desired polishing endpoint can be improved, and within-wafer and wafer-to-wafer thickness non-uniformity (WIWNU and WTWNU) can be reduced.

The details of one or more embodiments are set forth in the accompanying drawings and the description below. Other features, aspects, and advantages will become apparent from the description, the drawings, and the claims.

BRIEF DESCRIPTION OF THE DRAWINGS

FIG. 1 illustrates distortion in measured spectra as a polishing pad ages.

FIG. 5A is a flow diagram of a method of generating reference spectra.

FIG. 5B is a flow diagram of a method of generating transmission curves.

FIG. 6A illustrates a measured spectrum from the in-situ optical monitoring system.

FIG. 6B illustrates a library of reference spectra.

Like reference numbers and designations in the various drawings indicate like elements.

DETAILED DESCRIPTION

Figure 2:
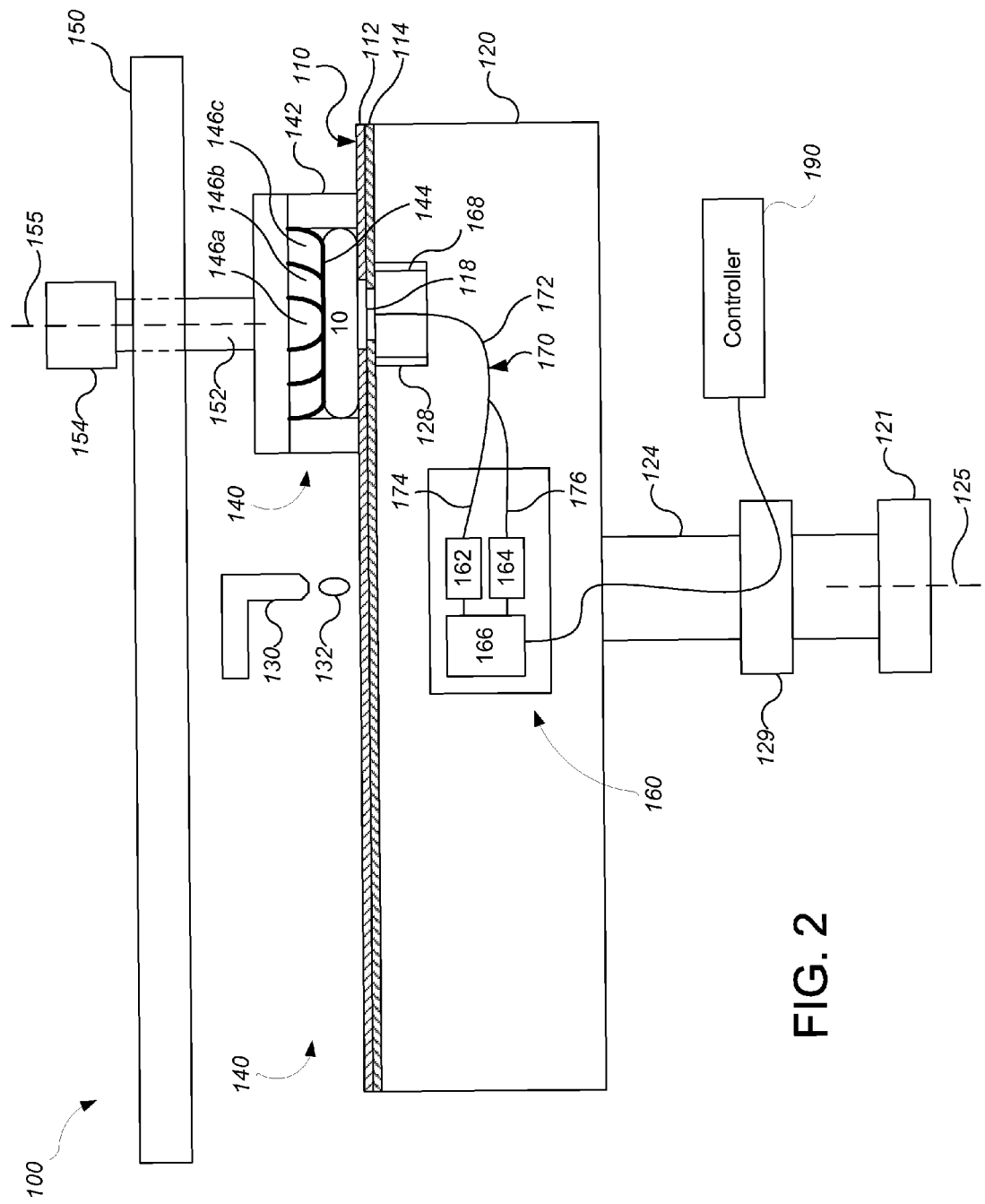
FIG. 2 illustrates a schematic cross-sectional view of an example of a polishing apparatus.

One optical monitoring technique is to measure spectra of light reflected from a substrate during polishing. These measured spectra can be used to generate a sequence of values which can be used to determine a polishing endpoint or an adjustment for a polishing rate. In some implementations, a matching reference spectra from a library is selected for each measured spectrum, and the sequence of values is generated from a value associated with each reference spectrum.

As noted above, transmission of the window in the polishing pad can change as the pad ages, and the transmission can be different from pad-to-pad. The change in transmission is not constant as a function of wavelength. In general, as the polishing pad ages, the transmission of light decreases toward the short wavelengths, e.g., the window becomes less transmissive to blue light as the window ages, wears or deforms. Without being limited to any particular theory, the change in transmission might be caused by the exposure of the pad window to UV light, by high temperature, by scratching from the substrate or polishing debris, or by mechanical deformation of the window which increase the amount of polishing liquid that pools between the window and the substrate.

Moreover, aging of the light source in the optical monitoring system, e.g., the xenon bulb, can cause changes in the spectrum measured by the optical monitoring system. For example, the bulb can emit less blue light as the bulb ages.

One or more libraries of reference spectra that incorporate the distortion caused by variation of components in the optical path before the substrate surface can be constructed and stored. The optical path "before the substrate surface" includes the light source of the optical monitoring system, the detector, and components between the substrate surface and the light source and/or detector, e.g., the window in the polishing pad, but not necessarily the substrate surface itself.

FIG. 1 is a graph 50 schematically illustrating distortion in the measured spectrum, in terms of ratio of measured intensity after some period of use versus the intensity for a "fresh" window (e.g., unused or used for less than a minute) as a function of wavelength. Curve 52a illustrates the ratio after 5 minutes of use of the pad, curve 52b illustrates the ratio after 4 hours of use of the pad, curve 52c illustrates the ratio after 8 hours of use of the pad, curve 52d illustrates the ratio after 12 hours of use of the pad, and curve 52e illustrates the ratio after 16 hours of use of the pad.

The change in intensity as a function of wavelength increases the likelihood that the incorrect reference spectrum is selected as the best match. One technique to address this problem is to build a library of reference spectra that incorporate the distortion that accumulates as the polishing pad ages. For example, a library can include multiple reference spectra with different reference spectra incorporating different amounts of distortion, or multiple different libraries can include reference spectra that incorporate different amounts of distortion.

The substrate can be as simple as a single dielectric layer disposed on a semiconductor layer, or can be have a significantly more complex layer stack. For example, the substrate can include a first layer and a second layer disposed over the second layer. The first layer can be a dielectric, e.g., an oxide, such as silicon dioxide, or a low-k material, such as carbon doped silicon dioxide, e.g., Black Diamond™ (from Applied Materials, Inc.) or Coral™ (from Novellus Systems, Inc.). The second layer can be a barrier layer of different composition than the first layer. For example, the barrier layer can be a metal or a metal nitride, e.g., tantalum nitride or titanium nitride. Optionally disposed between the first and second layers are one or more additional layers, e.g., a low-k capping material, e.g., a material formed from tetraethyl orthosilicate (TEOS). Both the first layer and the second layer are at least semi-transparent. Together, the first layer and one or more additional layers (if present) provide a layer stack below the second layer.

Chemical mechanical polishing can be used to planarize the substrate until the second layer is exposed. For example, if an opaque conductive material is present, it can be polished until the second layer, e.g., the barrier layer, is exposed. Then, the portion of the second layer remaining over the first layer is removed and the substrate is polished until the first layer, e.g., a dielectric layer, is exposed. In addition, it is sometimes desired to polish the first layer, e.g., the dielectric layer, until a target thickness remains or a target amount of material has been removed.

FIG. 2 illustrates an example of a polishing apparatus 100. The polishing apparatus 100 includes a rotatable disk-shaped platen 120 on which a polishing pad 110 is situated. The platen is operable to rotate about an axis 125. For example, a motor 121 can turn a drive shaft 124 to rotate the platen 120. The polishing pad 110 can be a two-layer polishing pad with an outer polishing layer 112 and a softer backing layer 114.

The polishing apparatus 100 can include a port 130 to dispense polishing liquid 132, such as a slurry, onto the polishing pad 110 to the pad. The polishing apparatus can also include a polishing pad conditioner to abrade the polishing pad 110 to maintain the polishing pad 110 in a consistent abrasive state.

The polishing apparatus 100 includes one or more carrier heads 140. Each carrier head 140 is operable to hold a substrate 10 against the polishing pad 110. Each carrier head 140 can have independent control of the polishing parameters, for example pressure, associated with each respective substrate.

Figure 3:
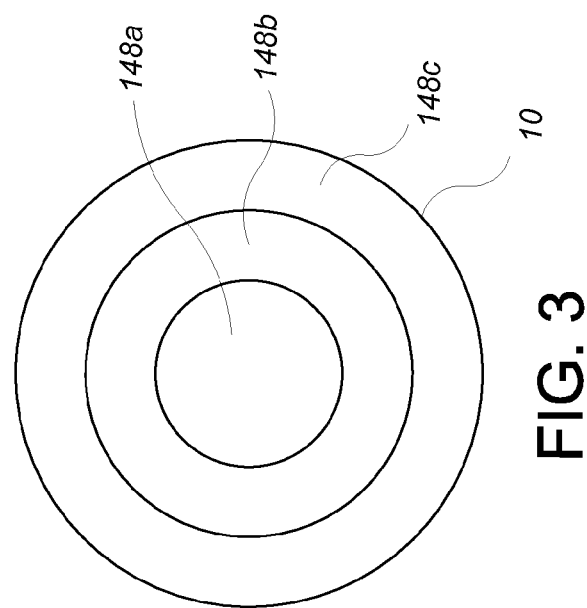
FIG. 3 illustrates a schematic top view of a substrate having multiple zones.

In particular, each carrier head 140 can include a retaining ring 142 to retain the substrate 10 below a flexible membrane 144. Each carrier head 140 also includes a plurality of independently controllable pressurizable chambers defined by the membrane, e.g., three chambers 146a-146c, which can apply independently controllable pressurizes to associated zones 148a-148c on the flexible membrane 144 and thus on the substrate 10 (see FIG. 3). Referring to FIG. 2, the center zone 148a can be substantially circular, and the remaining zones 148b-148e can be concentric annular zones around the center zone 148a. Although only three chambers are illustrated in FIGS. 2 and 3 for ease of illustration, there could be one or two chambers, or four or more chambers, e.g., five chambers.

Returning to FIG. 2, each carrier head 140 is suspended from a support structure 150, e.g., a carousel, and is connected by a drive shaft 152 to a carrier head rotation motor 154 so that the carrier head can rotate about an axis 155. Optionally each carrier head 140 can oscillate laterally, e.g., on sliders on the carousel 150; or by rotational oscillation of the carousel itself. In operation, the platen is rotated about its central axis 125, and each carrier head is rotated about its central axis 155 and translated laterally across the top surface of the polishing pad.

While only one carrier head 140 is shown, more carrier heads can be provided to hold additional substrates so that the surface area of polishing pad 110 may be used efficiently. Thus, the number of carrier head assemblies adapted to hold substrates for a simultaneous polishing process can be based, at least in part, on the surface area of the polishing pad 110.

The polishing apparatus also includes an in-situ optical monitoring system 160, e.g., a spectrographic monitoring system, which can be used to determine whether to adjust a polishing rate or an adjustment for the polishing rate as discussed below. An optical access through the polishing pad is provided by including an aperture (i.e., a hole that runs through the pad) or a solid window 118. The solid window 118 can be secured to the polishing pad 110, e.g., as a plug that fills an aperture in the polishing pad, e.g., is molded to or adhesively secured to the polishing pad, although in some implementations the solid window can be supported on the platen 120 and project into an aperture in the polishing pad.

The optical monitoring system 160 can include a light source 162, a light detector 164, and circuitry 166 for sending and receiving signals between a remote controller 190, e.g., a computer, and the light source 162 and light detector 164. One or more optical fibers can be used to transmit the light from the light source 162 to the optical access in the polishing pad, and to transmit light reflected from the substrate 10 to the detector 164. For example, a bifurcated optical fiber 170 can be used to transmit the light from the light source 162 to the substrate 10 and back to the detector 164. The bifurcated optical fiber an include a trunk 172 positioned in proximity to the optical access, and two branches 174 and 176 connected to the light source 162 and detector 164, respectively.

In some implementations, the top surface of the platen can include a recess 128 into which is fit an optical head 168 that holds one end of the trunk 172 of the bifurcated fiber. The optical head 168 can include a mechanism to adjust the vertical distance between the top of the trunk 172 and the solid window 118.

The output of the circuitry 166 can be a digital electronic signal that passes through a rotary coupler 129, e.g., a slip ring, in the drive shaft 124 to the controller 190 for the optical monitoring system. Similarly, the light source can be turned on or off in response to control commands in digital electronic signals that pass from the controller 190 through the rotary coupler 129 to the optical monitoring system 160. Alternatively, the circuitry 166 could communicate with the controller 190 by a wireless signal.

The light source 162 can be operable to emit white light. In one implementation, the white light emitted includes light having wavelengths of 200-800 nanometers. A suitable light source is a xenon lamp or a xenon mercury lamp.

The light detector 164 can be a spectrometer. A spectrometer is an optical instrument for measuring intensity of light over a portion of the electromagnetic spectrum. A suitable spectrometer is a grating spectrometer. Typical output for a spectrometer is the intensity of the light as a function of wavelength (or frequency).

As noted above, the light source 162 and light detector 164 can be connected to a computing device, e.g., the controller 190, operable to control their operation and receive their signals. The computing device can include a microprocessor situated near the polishing apparatus, e.g., a programmable computer. With respect to control, the computing device can, for example, synchronize activation of the light source with the rotation of the platen 120.

In some implementations, the light source 162 and detector 164 of the in-situ monitoring system 160 are installed in and rotate with the platen 120. In this case, the motion of the platen will cause the sensor to scan across each substrate. In particular, as the platen 120 rotates, the controller 190 can cause the light source 162 to emit a series of flashes starting just before and ending just after the optical access passes below the substrate 10. Alternatively, the computing device can cause the light source 162 to emit light continuously starting just before and ending just after each substrate 10 passes over the optical access. In either case, the signal from the detector can be integrated over a sampling period to generate spectra measurements at a sampling frequency.

In operation, the controller 190 can receive, for example, a signal that carries information describing a spectrum of the light received by the light detector for a particular flash of the light source or time frame of the detector. Thus, this spectrum is a spectrum measured in-situ during polishing.

Figure 4:
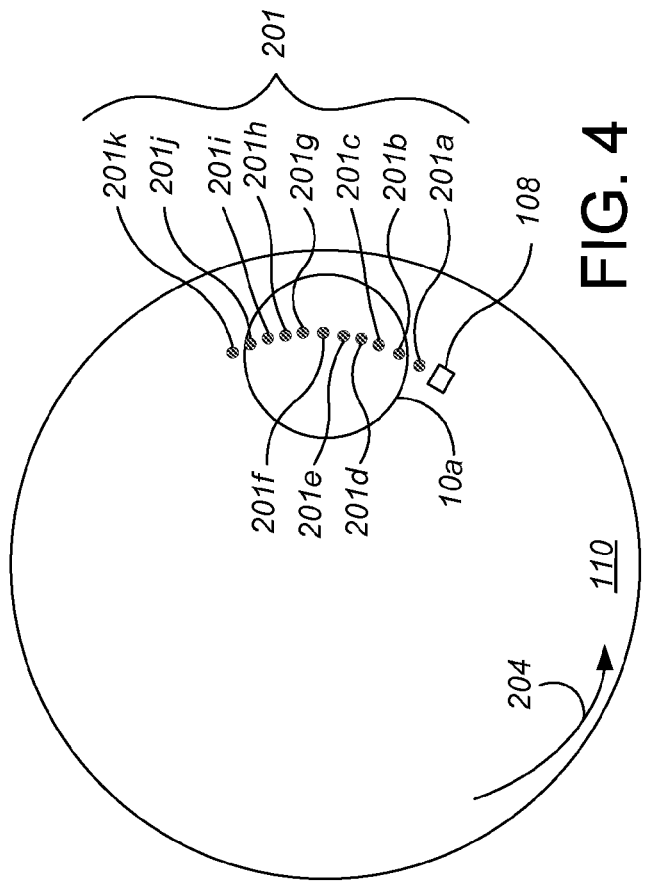
FIG. 4 illustrates a top view of a polishing pad and shows locations where in-situ measurements are taken on a substrate.

As shown by in FIG. 4, if the detector is installed in the platen, due to the rotation of the platen (shown by arrow 204), as the window 108 travels below a carrier head, the optical monitoring system making spectra measurements at a sampling frequency will cause the spectra measurements to be taken at locations 201 in an arc that traverses the substrate 10. For example, each of points 201a-201k represents a location of a spectrum measurement by the monitoring system (the number of points is illustrative; more or fewer measurements can be taken than illustrated, depending on the sampling frequency). The sampling frequency can be selected so that between five and twenty spectra are collected per sweep of the window 108. For example, the sampling period can be between 3 and 100 milliseconds.

As shown, over one rotation of the platen, spectra are obtained from different radii on the substrate 10. That is, some spectra are obtained from locations closer to the center of the substrate 10 and some are closer to the edge. Thus, for any given scan of the optical monitoring system across a substrate, based on timing, motor encoder information, and optical detection of the edge of the substrate and/or retaining ring, the controller 190 can calculate the radial position (relative to the center of the substrate being scanned) for each measured spectrum from the scan. The polishing system can also include a rotary position sensor, e.g., a flange attached to an edge of the platen that will pass through a stationary optical interrupter, to provide additional data for determination of which substrate and the position on the substrate of the measured spectrum. The controller can thus associate the various measured spectra with the controllable zones 148b-148e (see FIG. 2) on the substrates 10a and 10b. In some implementations, the time of measurement of the spectrum can be used as a substitute for the exact calculation of the radial position.

Over multiple rotations of the platen, for each zone, a sequence of spectra can be obtained over time. Without being limited to any particular theory, the spectrum of light reflected from the substrate 10 evolves as polishing progresses (e.g., over multiple rotations of the platen, not during a single sweep across the substrate) due to changes in the thickness of the outermost layer, thus yielding a sequence of time-varying spectra. Moreover, particular spectra are exhibited by particular thicknesses of the layer stack.

In some implementations, the controller, e.g., the computing device, can be programmed to compare a measured spectrum to multiple reference spectra and to determine which reference spectrum provides the best match. In particular, the controller can be programmed to compare each spectrum from a sequence of measured spectra from each zone to multiple reference spectra to generate a sequence of best matching reference spectra for each zone.

As used herein, a reference spectrum is a predefined spectrum generated prior to polishing of the substrate. A reference spectrum can have a pre-defined association, i.e., defined prior to the polishing operation, with a value representing a time in the polishing process at which the spectrum is expected to appear, assuming that the actual polishing rate follows an expected polishing rate. Alternatively or in addition, the reference spectrum can have a pre-defined association with a value of a substrate property, such as a thickness of the outermost layer.

A reference spectrum can be generated empirically, e.g., by measuring the spectra from a test substrate, e.g., a test substrate having a known initial layer thicknesses. For example, to generate a plurality of reference spectra, a set-up substrate is polished using the same polishing parameters that would be used during polishing of device wafers while a sequence of spectra are collected. For each spectrum, a value is recorded representing the time in the polishing process at which the spectrum was collected. For example, the value can be an elapsed time, or a number of platen rotations. The substrate can be overpolished, i.e., polished past a desired thickness, so that the spectrum of the light that reflected from the substrate when the target thickness is achieved can be obtained.

In order to associate each spectrum with a value of a substrate property, e.g., a thickness of the outermost layer, the initial spectra and property of a "set-up" substrate with the same pattern as the product substrate can be measured pre-polish at a metrology station. The final spectrum and property can also be measured post-polish with the same metrology station or a different metrology station. The properties for spectra between the initial spectra and final spectra can be determined by interpolation, e.g., linear interpolation based on elapsed time at which the spectra of the test substrate was measured.

In addition to being determined empirically, some or all of the reference spectra can be calculated from theory, e.g., using an optical model of the substrate layers. For example, and optical model can be used to calculate a reference spectrum for a given outer layer thickness D. A value representing the time in the polishing process at which the reference spectrum would be collected can be calculated, e.g., by assuming that the outer layer is removed at a uniform polishing rate. For example, the time Ts for a particular reference spectrum can be calculated simply by assuming a starting thickness D0 and uniform polishing rate R (Ts=(D0−D)/R). As another example, linear interpolation between measurement times T1, T2 for the pre-polish and post-polish thicknesses D1, D2 (or other thicknesses measured at the metrology station) based on the thickness D used for the optical model can be performed (Ts=T2−T1*(D1−D)/(D1−D2)).

In some implementations, software can be used to automatically calculate multiple reference spectra. Since there are variations in the thicknesses of the underlying layers of the incoming substrates, the manufacturer can input a thickness range and a thickness increment for at least one of the underlying layers, e.g., for multiple underlying layers. The software will calculate a reference spectra for each combination of thicknesses of the underlying layers. Multiple reference spectra can be calculated for each thickness of the overlying layer.

To calculate the reference spectra, the following optical model can be used. The reflectance $R_{STACK}$ of the top layer p of a thin film stack can be calculated as $$R_{STACK} = \left| \frac{E_p^-}{E_p^+} \right|^2$$

where $E_p^+$ represents the electro-magnetic field strength of the incoming light beam and $E_p^-$ represents the electromagnetic field strength of the outgoing light beam.

The values $E_p^+$ and $E_p^-$ can be calculated as $$E_p^+ = (E_p + H_p/\mu_p)/2 \quad E_p^- = (E_p - H_p/\mu_p)/2$$

The fields E and H in an arbitrary layer j can be calculated using transfer-matrix methods from the fields E and H in an underlying layer. Thus, in a stack of layers 0, 1, ..., p−1, p (where layer 0 is the bottom layer and layer p is the outermost layer), for a given layer j>0, $E_j$ and $H_j$ can be calculated as $$\begin{bmatrix} E_j \\ H_j \end{bmatrix} = \begin{bmatrix} \cos g_j & \frac{1}{u_j}\sin g_j \\ i\mu_j \sin g_j & \cos g_j \end{bmatrix} \begin{bmatrix} E_{j-1} \\ H_{j-1} \end{bmatrix}$$

with $\mu_j=(n_j-ik_j)\cdot\cos\phi_j$ and $g_j=2\pi(n_j-ik_j)\cdot t_j\cdot\cos\phi_j/\lambda$, where $n_j$ is the index of refraction of layer j, $k_j$ is an extinction coefficient of layer j, $t_j$ is the thickness of layer j, $\phi_j$ is the incidence angle of the light to layer j, and $\lambda$ is the wavelength. For the bottom layer in the stack, i.e., layer j=0, $E_0=1$ and $H_0=\mu_0=(n_0-ik_0)\cdot\cos\phi_0$. The index of refraction n and the extinction coefficient k for each layer can be determined from scientific literature, and can be functions of wavelength. The incidence angle $\phi$ can be calculated from Snell's law.

The thickness t for a layer can be calculated from the thickness range and thickness increment input by the user for the layer, e.g., $t_j=T_{MINj}+k^*T_{INCj}$ for k=0, 1, ..., for $t_j \leq T_{MAXj}$, where $T_{MINj}$ and $T_{MAXj}$ are the lower and upper boundaries of the range of thicknesses for layer j and $T_{INCj}$ is the thickness increment for layer j. The calculation can be iterated for each combination of thickness values of the layers.

A potential advantage of this technique is quick generation of a large number of reference spectra that can correspond to different combinations of thicknesses of layers on the substrate, thus improving likelihood of finding a good matching reference spectra and improving accuracy and reliability of the optical monitoring system.

In addition to variations of the layer thicknesses, the optical model can include variations in the spectral contribution of the metal layer. That is, depending on the pattern on the die being manufactured, some spectral measurements may be made in regions with high concentration of metal (e.g., from metal material 28 in the trenches), whereas other spectral measurements may be made in regions with lower concentration of metal.

The spectrum $R_{LIBRARY}$ that is added to the library ban be calculated as $$R_{LIBRARY} = \frac{R_{STACK}}{R_{BASELINE}}(1-X) + X*R_{Metal}$$

Where $R_{BASELINE}$ is the spectral reflectance of the material at the bottom of the optical stack, e.g., bare semiconductor, e.g., for a substrate in a front-end-of-line process, or bare metal, e.g., for a substrate in a back-end-of-line process. The bare semiconductor can be the reflectance off of bare silicon; the bare metal can be copper. X is the percentage contribution to the spectrum of the metal, e.g., copper, and $R_{Metal}$ is the reflectance spectrum from the metal, e.g., copper. In some implementations, e.g., if the metal layer 14 and the metal material 28 are the same material, e.g., copper, then $R_{BASELINE}$ and $R_{Metal}$ are the same spectrum, e.g., the spectrum for copper. The calculation of spectrum $R_{LIBRARY}$ can be iterated over multiple values for X. For example, X can vary between 0.0 and 1.0 at 0.2 intervals. A potential advantage of this technique is generation of reference spectra that can correspond to different concentrations of metal in the measured spot on the substrate, thus improving likelihood of finding a good matching reference spectra and improving accuracy and reliability of the optical monitoring system.

Whether generated empirically or calculated from theory, at least one reference spectrum is stored in a computer system. This computer system may be the controller 190, or a different computer system.

For some types of substrates, e.g., some layer structures and die patterns, the techniques described above for generation of a library of reference spectra based on an optical model can be sufficient. However, for some types of substrates, the reference spectra based on this optical model do not correspond to empirically measured spectra. Without being limited to any particular theory, as additional layers are added to the stack on the substrate, scattering of light increases, e.g., from the different patterned metal layers on the substrate. In short, as the number of metal layers increases, it becomes less likely that light from lower layers on the substrate will be reflected back to enter the optical fiber and reach the detector.

In some implementations, to simulate the scattering caused by increasing numbers of metal layers, a modified extinction coefficient can be used in the optical model for calculation of the reference spectra. The modified extinction coefficient is larger than the natural extinction coefficient for the material of the layer. An amount added to the extinction coefficient can be larger for layers closer to the wafer.

For example, in the equations above, the terms $\mu_j$ and $g_j$ can be replaced by $\mu'_j$ and $g'_j$, respectively, with $\mu'_j$ and $g'_j$ calculated as $$\mu'_j=(n_j-i(k_j+m_j))\cdot\cos\phi_j \quad g'_j=2\pi(n_j-i(k_j+m_j))\cdot t_j\cdot\cos\phi_j/\lambda$$

where $m_j$ is an amount to increase the extinction coefficient of layer j. In general, $m_j$ is equal to or greater than 0, and can be up to 1. For layers near the top of the stack, $m_j$ can be small, e.g., 0. For deeper layers, $m_j$ can larger, e.g., 0.2, 0.4 or 0.6. The amount $m_j$ can increase monotonically as j decreases. The amount $m_j$ can be functions of wavelength, e.g., for a particular layer, $m_j$ can be greater at longer wavelengths or can be greater at shorter wavelengths.

FIG. 5A shows a method 80 of constructing a plurality of reference spectra, e.g., to create one or more libraries.

As noted above, transmission of the window 116 in the polishing pad 110 (see FIG. 2) can change as the polishing pad ages, and the light emitted by the light source 162 can changes as the bulb in the light source ages. A plurality of transmission curves is generated (step 82). The transmission curves represent distortion to a spectrum introduced by variations in components in an optical path before a substrate surface. For example, the different transmission curves can represent distortion introduced by aging of components of the polishing system, e.g., at different times in the life of the polishing pad and/or bulb of the light source. As another example, different transmission curves can represent distortion introduced by differences between components of the polishing system, e.g., window-to-window and/or bulb-to-bulb differences. A plurality of different transmission curves can be stored in a computer system. A transmission curve can be stored as a ratio between 0 and 1 as a function of wavelength.

One approach to generate the transmission curves is empirical. In particular, referring to FIG. 5B, a base spectrum is obtained from a test substrate, e.g., a blank substrate, e.g., a bare silicon or bare copper substrate, using the in-situ optical monitoring system (step 90). The base spectrum can be obtained at the beginning of life of a polishing pad 110 and a bulb of the light source 162. One or more additional spectra are obtained, again using the in-situ optical monitoring system (step 92), and using a test substrate of the same material (or the same test substrate), but at different times during the life of the polishing pad 110 and/or bulb. For example, the spectra could be obtained by measuring the test substrate after 5 minutes of use of the pad, after 4 hours of use of the pad, after 8 hours of use of the pad, after 12 hours of use of the pad, and after 16 hours of use of the pad.

Optionally, a spectrum can also be measured by the in situ monitoring system under a dark condition (i.e., when no substrate is being measured by the in situ monitoring system) at the same time in the pad life that the base spectrum and each additional spectrum is measured.

The transmission curve can then be calculated from the base spectrum and the additional spectrum (step 94). For example, a transmission curve can be calculated for each additional spectrum. A transmission curve can be calculated by a division operation in which the additional spectrum is in the numerator and the base spectrum is in the denominator. In particular, the transmission curve T can be calculated as $$T = \frac{A - D_A}{B - D_B}$$

where A is the additional spectrum, $D_A$ is the spectrum received by the in situ monitoring system under the dark condition at the same time in the pad life as the additional spectrum, B is the base spectrum, and $D_B$ is the spectrum received by the in situ monitoring system under the dark condition at the same time in the pad life as the base spectrum.

At least some of the transmission curves are stored. However, it may not be necessary to store all of the transmission curves T that are calculated. For example, some transmission curves that are substantially similar to existing transmission curves could be discarded.

Alternatively, rather than store the empirically generated transmission curves, transmission curves can be generated from a model. For example, a Cauchy equation or a $3^{rd}$ order polynomial can be used to model the transmission curve. The polynomial coefficients can be selected, e.g., using a fitting procedure, so that the so that Cauchy equation or a $3^{rd}$ order polynomial follows the empirically generated transmission curve.

At least one reference spectrum is generated (step 84), e.g., either empirically or from theory as discussed above. The at least one reference spectrum can be generated before or after the transmission curves are generated.

Then, for at least two transmission curves from the plurality of different transmission curves, a modified reference spectrum is calculated in a computer system from the reference spectrum and the transmission curve to generate a plurality of modified reference spectra. In some implementations, the computer system can receive user input identifying the at least two transmission curves from the plurality of different transmission curves. The computer at which the calculation is performed need not be the same computer at which the at least one reference spectrum was generated or the same computer at which the transmission curves were generated; the at least one reference spectrum and/or the transmission curves can be received electronically.

In some implementations, for each stored transmission curve, the at least one reference spectrum is multiplied by the stored transmission curve to generate a plurality of modified reference spectra (step 86), which can be added to the same or a different library as the original at least one reference spectrum. These modified reference spectra are then stored, e.g., in the controller 190, as the reference spectra to be used in the optical monitoring procedure. Assuming that the modified reference spectra are added to the same library as the at least one reference spectrum, this will increase the library in size by a factor of the number of transmission curves. For example, if the original library contained 100 reference spectra, and the number of transmission curves is 3, then the new library size is now 400 spectra (100 original spectra plus 300 normalized spectra).

Referring to FIGS. 6A and 6B, a measured spectrum 300 (see FIG. 5A) can be compared to reference spectra 320 from one or more libraries 310 (see FIG. 5B). As used herein, a library of reference spectra is a collection of reference spectra which represent substrates that share a property in common. However, the property shared in common in a single library may vary across multiple libraries of reference spectra. For example, two different libraries can include reference spectra that represent substrates with two different underlying thicknesses. For a given library of reference spectra, variations in the upper layer thickness, rather than other factors (such as differences in wafer pattern, underlying layer thickness, or layer composition), can be primarily responsible for the differences in the spectral intensities. In some implementations, a given library of reference spectra, differences in the spectral intensities can be due to variations in the upper layer thickness and variations in the transmission curve used to generate the reference spectra. In some implementations, a given library of reference spectra, differences in the spectral intensities can be primarily due to variations in the transmission curve used to generate the reference spectra.

Because the plurality of spectra spans the likely range of influence of the window, it is more likely that a proper match will be found. Thus, the resulting library or libraries of reference spectra enable the matching algorithm to remain reliable when there is variation in transmission of the window. Thus, reliability of the endpoint system to detect a desired polishing endpoint can be improved, and within-wafer and wafer-to-wafer thickness non-uniformity (WIWNU and WTWNU) can be reduced.

Reference spectra 320 for different libraries 310 can be generated by polishing multiple "set-up" substrates with different substrate properties (e.g., underlying layer thicknesses, or layer composition) and collecting spectra as discussed above; the spectra from one set-up substrate can provide a first library and the spectra from another substrate with a different underlying layer thickness can provide a second library. Alternatively or in addition, reference spectra for different libraries can be calculated from theory, e.g., spectra for a first library can be calculated using the optical model with the underlying layer having a first thickness, and spectra for a second library can be calculated using the optical model with the underlying layer having a different one thickness.

In some implementations, each reference spectrum 320 is assigned an index value 330. In general, each library 310 can include many reference spectra 320, e.g., one or more, e.g., exactly one, reference spectra for each platen rotation over the expected polishing time of the substrate. This index 330 can be the value, e.g., a number, representing the time in the polishing process at which the reference spectrum 320 is expected to be observed. The spectra can be indexed so that each spectrum in a particular library has a unique index value. The indexing can be implemented so that the index values are sequenced in an order in which the spectra of a test substrate were measured. An index value can be selected to change monotonically, e.g., increase or decrease, as polishing progresses. In particular, the index values of the reference spectra can be selected so that they form a linear function of time or number of platen rotations (assuming that the polishing rate follows that of the model or test substrate used to generate the reference spectra in the library). For example, the index value can be proportional, e.g., equal, to a number of platen rotations at which the reference spectra was measured for the test substrate or would appear in the optical model. Thus, each index value can be a whole number. The index number can represent the expected platen rotation at which the associated spectrum would appear.

The reference spectra and their associated index values can be stored in a reference library. For example, each reference spectrum 320 and its associated index value 330 can be stored in a record 340 of database 350. The database 350 of reference libraries of reference spectra can be implemented in memory of the computing device of the polishing apparatus.

As noted above, for each zone of each substrate, based on the sequence of measured spectra or that zone and substrate, the controller 190 can be programmed to generate a sequence of best matching spectra. A best matching reference spectrum can be determined by comparing a measured spectrum to the reference spectra from a particular library.

In some implementations, the best matching reference spectrum can be determined by calculating, for each reference spectrum, a sum of squared differences between the measured spectrum and the reference spectrum. The reference spectrum with the lowest sum of squared differences has the best fit. Other techniques for finding a best matching reference spectrum are possible, e.g., lowest sum of absolute differences.

In some implementations, the best matching reference spectrum can be determined by using a matching technique other than sum of squared differences. In one implementation, for each reference spectrum, a cross-correlation between the measured spectrum and the reference spectrum is calculated, and the reference spectrum with the greatest correlation is selected as the matching reference spectrum. A potential advantage of cross-correlation is that it is less sensitive to lateral shift of a spectrum, and thus can be less sensitive to underlying thickness variation. In order to perform the cross-correlation, the leading and trailing ends of the measured spectrum can be padded with "zeros" to provide data to compare against the reference spectrum as the reference spectrum is shifted relative to the measured spectrum. Alternatively, the leading end of the measured spectrum can be padded with values equal to the value at the leading edge of the measured spectrum, and the trailing end of the measured spectrum can be padded with values equal to the value at the trailing edge of the measured spectrum. Fast Fourier transforms can be used to increase the speed of calculation of the cross-correlation for real-time application of the matching technique.

In another implementation, a sum of enclidean vector distances, e.g., $D=1/(\lambda a-\lambda b)\cdot[\Sigma_{\lambda=\lambda a\ to\ \lambda b}|I_M(\lambda)^2-I_R(\lambda)^2|]$, where $\lambda a$ to $\lambda b$ is wavelength summed over, calculated, $I_M(\lambda)$ is the measured spectrum, and $I_R(\lambda)$ is the reference spectrum. In another implementation, for each reference spectrum, a sum of derivative differences, e.g., $D=1/(\lambda a-\lambda b)\cdot[\Sigma_{\lambda=\lambda a\ to\ \lambda b}|dI_M(\lambda)/d\lambda-dI_R(\lambda)/d\lambda|]$, and the reference spectrum with the lowest sum is selected as the matching reference spectrum.

A method that can be applied to decrease computer processing is to limit the portion of the library that is searched for matching spectra. The library typically includes a wider range of spectra than will be obtained while polishing a substrate. During substrate polishing, the library searching is limited to a predetermined range of library spectra. In some embodiments, the current rotational index N of a substrate being polished is determined. For example, in an initial platen rotation, N can be determined by searching all of the reference spectra of the library. For the spectra obtained during a subsequent rotation, the library is searched within a range of freedom of N. That is, if during one rotation the index number is found to be N, during a subsequent rotation which is X rotations later, where the freedom is Y, the range that will be searched from (N+X)−Y to (N+X)+Y.

Figure 7:
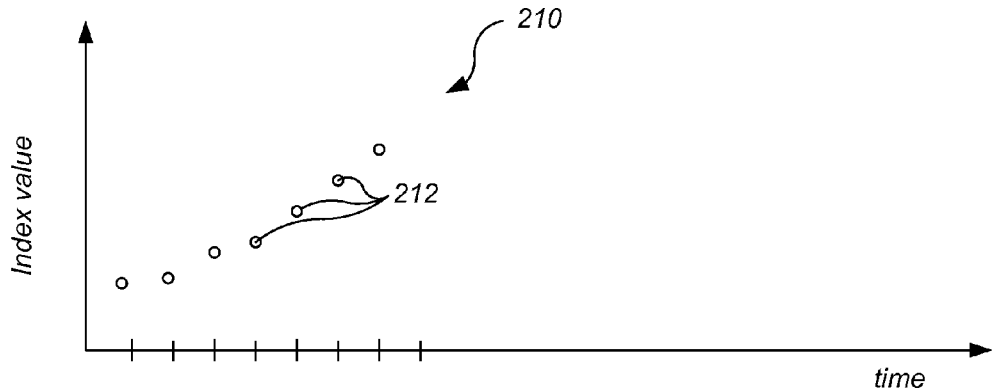
FIG. 7 illustrates an index trace.

Referring to FIG. 7, which illustrates the results for only a single zone of a single substrate, the index value of each of the best matching spectra in the sequence can be determined to generate a time-varying sequence of index values 212. This sequence of index values can be termed an index trace 210. In some implementations, an index trace is generated by comparing each measured spectrum to the reference spectra from exactly one library. In general, the index trace 210 can include one, e.g., exactly one, index value per sweep of the optical monitoring system below the substrate.

For a given index trace 210, where there are multiple spectra measured for a particular zone in a single sweep of the optical monitoring system (termed "current spectra"), a best match can be determined between each of the current spectra and the reference spectra of one or more, e.g., exactly one, library. In some implementations, each selected current spectra is compared against each reference spectra of the selected library or libraries. Given current spectra e, f, and g, and reference spectra E, F, and G, for example, a matching coefficient could be calculated for each of the following combinations of current and reference spectra: e and E, e and F, e and G, f and E, f and F, f and G, g and E, g and F, and g and G. Whichever matching coefficient indicates the best match, e.g., is the smallest, determines the best-matching reference spectrum, and thus the index value. Alternatively, in some implementations, the current spectra can be combined, e.g., averaged, and the resulting combined spectrum is compared against the reference spectra to determine the best match, and thus the index value.

In some implementations, for at least some zones of some substrates, a plurality of index traces can be generated. For a given zone of a given substrate, an index trace can be generated for each reference library of interest. That is, for each reference library of interest to the given zone of the given substrate, each measured spectrum in a sequence of measured spectra is compared to reference spectra from a given library, a sequence of the best matching reference spectra is determined, and the index values of the sequence of best matching reference spectra provide the index trace for the given library.

In summary, each index trace includes a sequence 210 of index values 212, with each particular index value 212 of the sequence being generated by selecting the index of the reference spectrum from a given library that is the closest fit to the measured spectrum. The time value for each index of the index trace 210 can be the same as the time at which the measured spectrum was measured.

If an overlying second layer is present, an in-situ monitoring technique can be used to detect clearing of the second layer and exposure of the underlying layer or layer structure. For example, exposure of the first layer at a time TC can be detected by a sudden change in the motor torque or total intensity of light reflected from the substrate, or from dispersion of the collected spectra as discussed in greater detail below.

Figure 8:
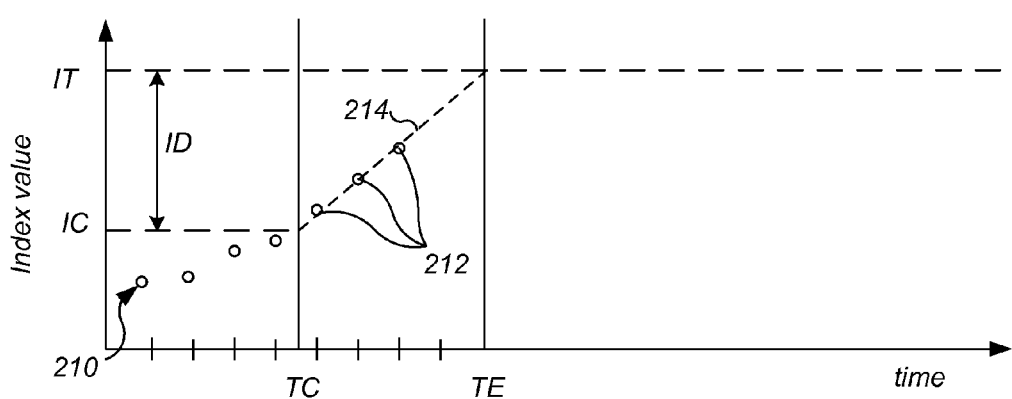
FIG. 8 illustrates an index trace having a linear function fit to index values collected after clearance of an overlying layer is detected.

As shown in FIG. 8, a function, e.g., a polynomial function of known order, e.g., a first-order function (e.g., a line 214) is fit, e.g., using robust line fitting, to the sequence of index values of spectra, e.g., the index values collected after time TC. Index values for spectra collected before the time TC can be ignored when fitting the function to the sequence of index values. Other functions can be used, e.g., polynomial functions of second-order, but a line provides ease of computation. Polishing can be halted at an endpoint time TE that the line 214 crosses a target index IT.

Figure 9:
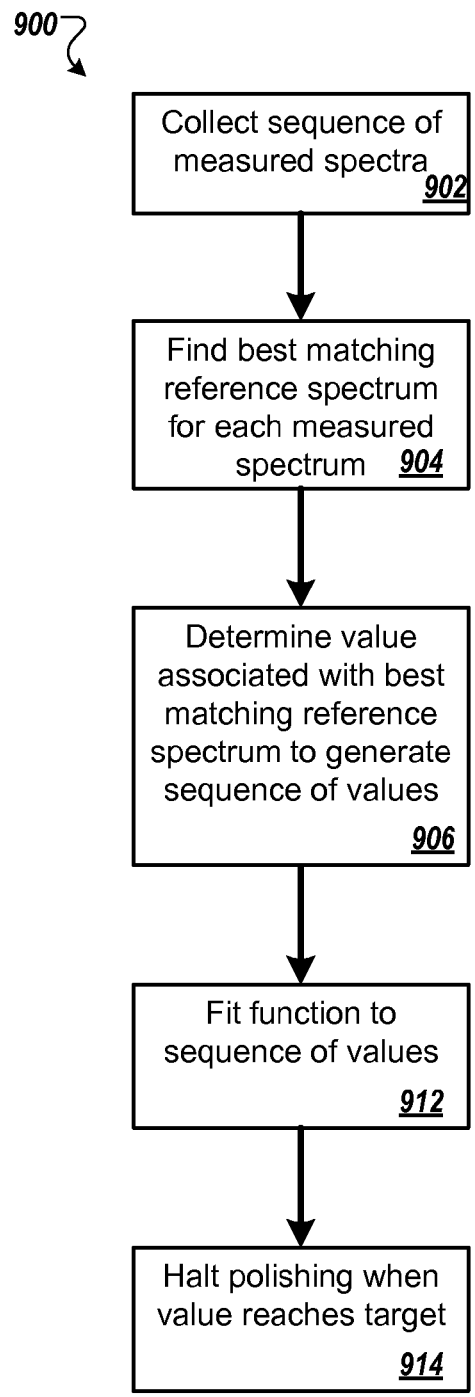
FIG. 9 is a flow diagram of an example process for fabricating a substrate and detecting a polishing endpoint.

FIG. 9 shows a flow chart of a method 900 of polishing a product substrate. The product substrate can have at least the same layer structure (but not necessarily layer thicknesses) and the same pattern, as the test substrates used to generate the reference spectra of the library.

A sequence of measured spectra are collected during polishing (step 902), e.g., using the in-situ monitoring system described above.

The measured spectra are analyzed to generate a sequence of values, and a function can be fit to the sequence of values. In particular, for each measured spectrum in the sequence of measured spectra, the a best matching reference spectra from a plurality of reference spectra is found (step 904). The value associated with the best matching reference spectrum is determined (step 906). Since there are a sequence of measured spectra, there is a sequence of best matching reference spectra, and thus a sequence of values. A function, e.g., a linear function or second-order or higher polynomial function, is fit to the sequence of values (step 912). In some implementations, values collected before a time TC, e.g., a time at which clearance of the second layer is detected, are not used in the calculation of the function.

Polishing can be halted once the value (e.g., a calculated value generated from the function fit to the sequence of values) reaches a target value (step 914). The target value IT can be set by the user prior to the polishing operation and stored. Alternatively, a target amount to remove can be set by the user, and a target value IT can be calculated from the target amount to remove. For example, a difference ID can be calculated from the target amount to remove, e.g., from an empirically determined ratio of amount removed to the value (e.g., the polishing rate), and adding the difference ID to the index value IC at the time TC that clearance of the overlying layer is detected (see FIG. 8).

It is also possible to use the function fit to the index values to adjust the polishing parameters, e.g., to adjust the polishing rate of one or more zones on a substrate to improve polishing uniformity. Alternatively, in some implementations, no function is fit to the sequence, and the values are themselves used to detect the polishing endpoint, e.g., by comparison to a target value.

Figure 10:
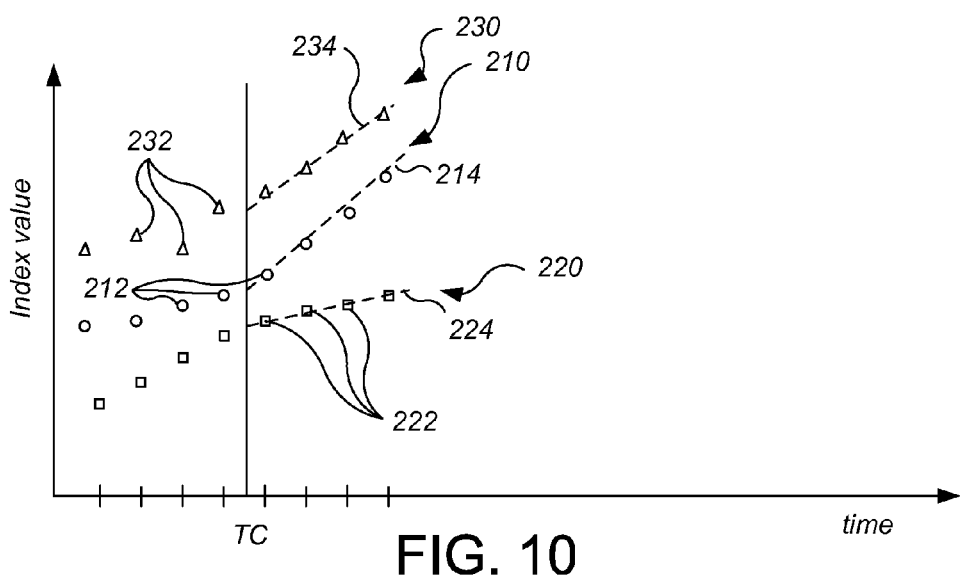
FIG. 10 illustrates a plurality of index traces.

Referring to FIG. 10, a plurality of index traces is illustrated. As discussed above, an index trace can be generated for each zone. For example, a first sequence 210 of index values 212 (shown by hollow circles) can be generated for a first zone, a second sequence 220 of index values 222 (shown by hollow squares) can be generated for a second zone, and a third sequence 230 of index values 232 (shown by hollow triangles) can be generated for a third zone. Although three zones are shown, there could be two zones or four or more zones. All of the zones can be on the same substrate, or some of the zones can be from different substrates being polished simultaneously on the same platen.

As discussed above, an in-situ monitoring technique can be used to detect clearing of the second layer and exposure of the underlying layer or layer structure. For example, exposure of the first layer at a time TC can be detected by a sudden change in the motor torque or total intensity of light reflected from the substrate, or from dispersion of the collected spectra as discussed in greater detail below.

For each substrate index trace, a polynomial function of known order, e.g., a first-order function (e.g., a line) is fit to the sequence of index values of spectra (which optionally can be limited to values collected after time TC) for the associated zone, e.g., using robust line fitting. For example, a first line 214 can be fit to index values 212 for the first zone, a second line 224 can be fit to the index values 222 of the second zone, and a third line 234 can be fit to the index values 232 of the third zone. Fitting of a line to the index values can include calculation of the slope S of the line and an x-axis intersection time T at which the line crosses a starting index value, e.g., 0. The function can be expressed in the form $I(t)=S \cdot (t-T)$, where t is time. The x-axis intersection time T can have a negative value, indicating that the starting thickness of the substrate layer is less than expected. Thus, the first line 214 can have a first slope S1 and a first x-axis intersection time T1, the second line 224 can have a second slope S2 and a second x-axis intersection time T2, and the third line 234 can have a third slope S3 and a third x-axis intersection time T3.

At some during the polishing process, e.g., at a time T0, a polishing parameter for at least one zone is adjusted to adjust the polishing rate of the zone of the substrate such that at a polishing endpoint time, the plurality of zones are closer to their target thickness than without such adjustment. In some embodiments, each zone can have approximately the same thickness at the endpoint time.

Figure 11:
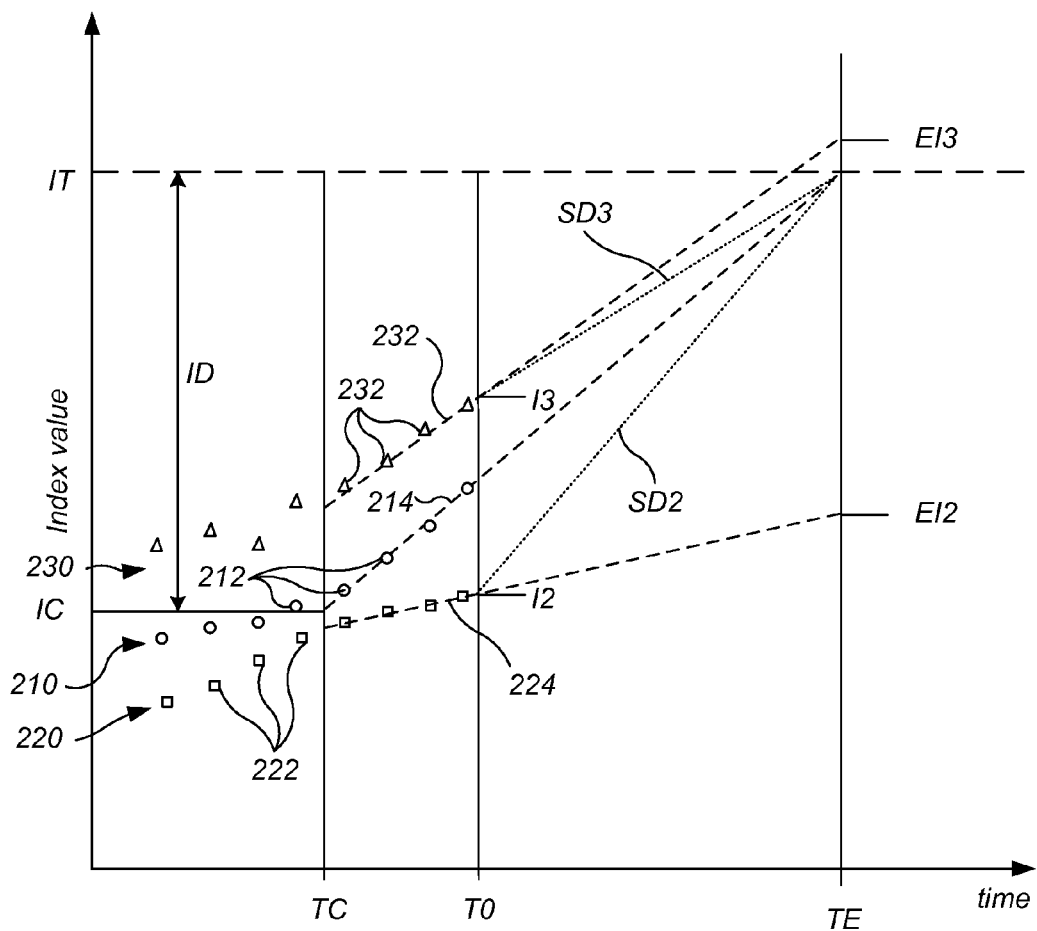
FIG. 11 illustrates a calculation of a plurality of desired slopes for a plurality of adjustable zones based on a time that an index trace of a reference zone reaches a target index.

Referring to FIG. 11, in some implementations, one zone is selected as a reference zone, and a projected endpoint time TE at which the reference zone will reach a target index IT is determined. For example, as shown in FIG. 11, the first zone is selected as the reference zone, although a different zone and/or a different substrate could be selected. The target thickness IT is set by the user prior to the polishing operation and stored. Alternatively, a target amount to remove TR can be set by the user, and a target index IT can be calculated from the target amount to remove TR. For example, an index difference ID can be calculated from the target amount to remove, e.g., from an empirically determined ratio of amount removed to the index (e.g., the polishing rate), and adding the index difference ID to the index value IC at the time TC that clearance of the overlying layer is detected.

In order to determine the projected time at which the reference zone will reach the target index, the intersection of the line of the reference zone, e.g., line 214, with the target index, IT, can be calculated. Assuming that the polishing rate does not deviate from the expected polishing rate through the remainder polishing process, then the sequence of index values should retain a substantially linear progression. Thus, the expected endpoint time TE can be calculated as a simple linear interpolation of the line to the target index IT, e.g., $IT=S \cdot (TE-T)$. Thus, in the example of FIG. 11 in which the first zone is selected as the reference zone, with associated first line 214, $IT=S1 \cdot (TE-T1)$, i.e., $TE=IT/S1-T1$.

One or more zones, e.g., all zones, other than the reference zone (including zones on other substrates) can be defined as adjustable zones. Where the lines for the adjustable zones meet the expected endpoint time TE define projected endpoint for the adjustable zones. The linear function of each adjustable zone, e.g., lines 224 and 234 in FIG. 11, can thus be used to extrapolate the index, e.g., EI2 and EI3, that will be achieved at the expected endpoint time ET for the associated zone. For example, the second line 224 can be used to extrapolate the expected index, EI2, at the expected endpoint time ET for the second zone, and the third line 234 can be used to extrapolate the expected index, EI3, at the expected endpoint time ET for the third zone.

As shown in FIG. 11, if no adjustments are made to the polishing rate of any of the zones after time T0, then if endpoint is forced at the same time for all zones, then each zone can have a different thickness (which is not desirable because it can lead to defects and loss of throughput).

If the target index will be reached at different times for different zones (or equivalently, the adjustable zones will have different expected indexes at the projected endpoint time of the reference zone), the polishing rate can be adjusted upwardly or downwardly, such that the zones would reach the target index (and thus target thickness) closer to the same time than without such adjustment, e.g., at approximately the same time, or would have closer to the same index value (and thus same thickness), at the target time than without such adjustment, e.g., approximately the same index value (and thus approximately the same thickness).

Thus, in the example of FIG. 11, commencing at a time T0, at least one polishing parameter for the second zone is modified so that the polishing rate of the zone is increased (and as a result the slope of the index trace 220 is increased). Also, in this example, at least one polishing parameter for the third zone is modified so that the polishing rate of the third zone is decreased (and as a result the slope of the index trace 230 is decreased). As a result the zones would reach the target index (and thus the target thickness) at approximately the same time (or if pressure to the zones halts at the same time, the zones will end with approximately the same thickness).

In some implementations, if the projected index at the expected endpoint time ET indicate that a zone of the substrate is within a predefined range of the target thickness, then no adjustment may be required for that zone. The range may be 2%, e.g., within 1%, of the target index.

The polishing rates for the adjustable zones can be adjusted so that all of the zones are closer to the target index at the expected endpoint time than without such adjustment. For example, a reference zone of the reference substrate might be chosen and the processing parameters for all of the other zone adjusted such that all of the zones will endpoint at approximately the projected time of the reference substrate. The reference zone can be, for example, a predetermined zone, e.g., the center zone 148a or the zone 148b immediately surrounding the center zone, the zone having the earliest or latest projected endpoint time of any of the zones of any of the substrates, or the zone of a substrate having the desired projected endpoint. The earliest time is equivalent to the thinnest substrate if polishing is halted at the same time. Likewise, the latest time is equivalent to the thickest substrate if polishing is halted at the same time. The reference substrate can be, for example, a predetermined substrate, a substrate having the zone with the earliest or latest projected endpoint time of the substrates. The earliest time is equivalent to the thinnest zone if polishing is halted at the same time. Likewise, the latest time is equivalent to the thickest zone if polishing is halted at the same time.

For each of the adjustable zones, a desired slope for the index trace can be calculated such that the adjustable zone reaches the target index at the same time as the reference zone. For example, the desired slope SD can be calculated from $(IT-I)=SD*(TE-T0)$, where I is the index value (calculated from the linear function fit to the sequence of index values) at time T0 polishing parameter is to be changed, IT is the target index, and TE is the calculated expected endpoint time. In the example of FIG. 11, for the second zone the desired slope SD2 can be calculated from $(IT-I2)=SD2*(TE-T0)$, and for the third zone the desired slope SD3 can be calculated from $(IT-I3)=SD3*(TE-T0)$.

Alternatively, in some implementations, there is no reference zone, and the expected endpoint time can be a predetermined time, e.g., set by the user prior to the polishing process, or can be calculated from an average or other combination of the expected endpoint times of two or more zones (as calculated by projecting the lines for various zones to the target index) from one or more substrates. In this implementation, the desired slopes are calculated substantially as discussed above, although the desired slope for the first zone of the first substrate must also be calculated, e.g., the desired slope SD1 can be calculated from $(IT-I1)=SD1*(TE'-T0)$.

Alternatively, in some implementations, there are different target indexes for different zones. This permits the creation of a deliberate but controllable non-uniform thickness profile on the substrate. The target indexes can be entered by user, e.g., using an input device on the controller. For example, the first zone of the substrate can have a first target index, the second zone of the substrate can have a second target index, and the third first zone of the substrate can have a third target index.

For any of the above methods described above, the polishing rate is adjusted to bring the slope of index trace closer to the desired slope. The polishing rates can be adjusted by, for example, increasing or decreasing the pressure in a corresponding chamber of a carrier head. The change in polishing rate can be assumed to be directly proportional to the change in pressure, e.g., a simple Prestonian model. For example, for each zone of each substrate, where zone was polished with a pressure Pold prior to the time T0, a new pressure Pnew to apply after time T0 can be calculated as Pnew=Pold*(SD/S), where S is the slope of the line prior to time T0 and SD is the desired slope.

For example, assuming that pressure Pold1 was applied to the first zone of the substrate, pressure Pold2 was applied to the second zone of the substrate, and pressure Pold3 was applied to the third zone of the substrate, then new pressure Pnew2 for the second zone of the substrate clan be calculated as Pnew2=Pold2*(SD2/S2), and the new pressure Pnew3 for the third zone of the substrate clan be calculated as Pnew3=Pold3*(SD3/S3).

The process of determining projected times that the substrates will reach the target thickness, and adjusting the polishing rates, can be performed just once during the polishing process, e.g., at a specified time, e.g., 40 to 60% through the expected polishing time, or performed multiple times during the polishing process, e.g., every thirty to sixty seconds. At a subsequent time during the polishing process, the rates can again be adjusted, if appropriate. During the polishing process, changes in the polishing rates can be made only a few times, such as four, three, two or only one time. The adjustment can be made near the beginning, at the middle or toward the end of the polishing process.

Polishing continues after the polishing rates have been adjusted, e.g., after time T0, the optical monitoring system continues to collect spectra for at least the reference zone and determine index values for the reference zone. In some implementations, the optical monitoring system continues to collect spectra and determine index values for each zone. Once the index trace of a reference zone reaches the target index, endpoint is called and the polishing operation stops.

Figure 12:
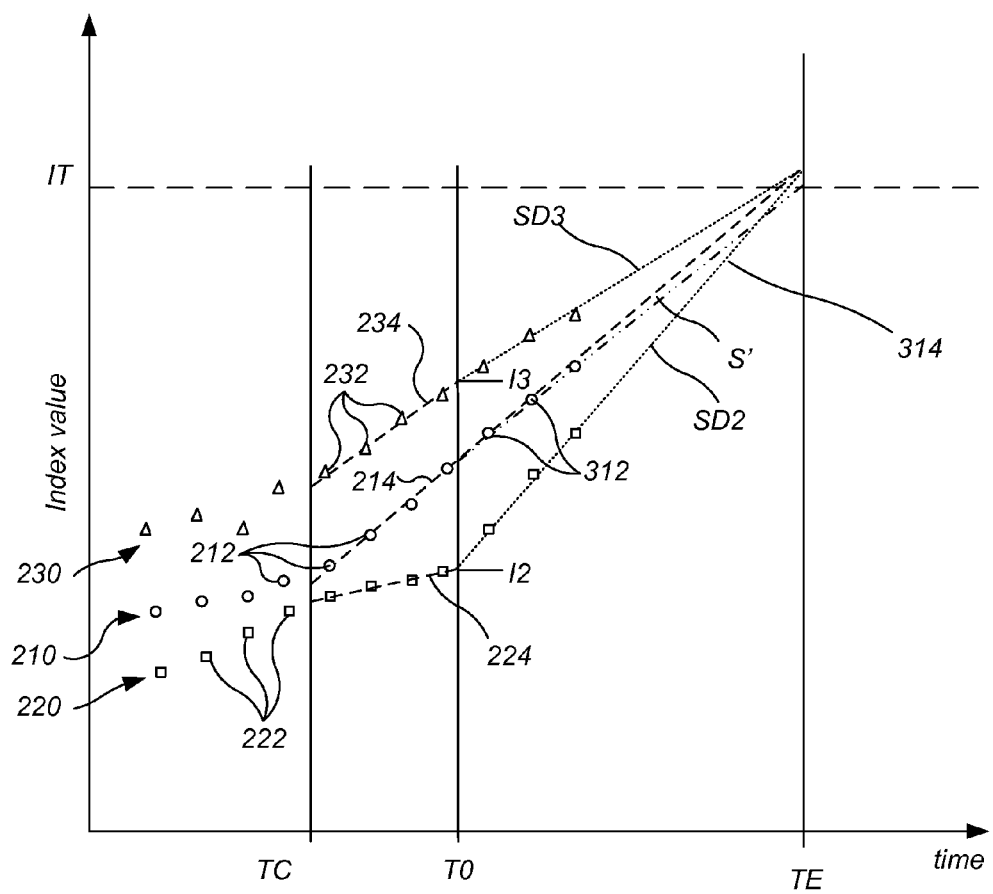
FIG. 12 illustrates a calculation of an endpoint for based on a time that an index trace of a reference zone reaches a target index.

For example, as shown in FIG. 12, after time T0, the optical monitoring system continues to collect spectra for the reference zone and determine index values 312 for the reference zone. If the pressure on the reference zone did not change (e.g., as in the implementation of FIG. 11), then the linear function can be calculated using data points from both before T0 (but not before TC) and after T0 to provide an updated linear function 314, and the time at which the linear function 314 reaches the target index IT indicates the polishing endpoint time. On the other hand, if the pressure on the reference zone changed at time T0, then a new linear function 314 with a slope S' can be calculated from the sequence of index values 312 after time T0, and the time at which the new linear function 314 reaches the target index IT indicates the polishing endpoint time. The reference zone used for determining endpoint can be the same reference zone used as described above to calculate the expected endpoint time, or a different zone (or if all of the zones were adjusted as described with reference to FIG. 11, then a reference zone can be selected for the purpose of endpoint determination). If the new linear function 314 reaches the target index IT slightly later (as shown in FIG. 12) or earlier than the projected time calculated from the original linear function 214, then one or more of the zones may be slightly overpolished or underpolished, respectively. However, since the difference between the expected endpoint time and the actual polishing time should be less than a couple seconds, this need not severely impact the polishing uniformity.

In some implementations, e.g., for copper polishing, after detection of the endpoint for a substrate, the substrate is immediately subjected to an overpolishing process, e.g., to remove copper residue. The overpolishing process can be at a uniform pressure for all zones of the substrate, e.g., 1 to 1.5 psi. The overpolishing process can have a preset duration, e.g., 10 to 15 seconds.

Where multiple index traces are generated for a particular zone, e.g., one index trace for each library of interest to the particular zone, then one of the index traces can be selected for use in the endpoint or pressure control algorithm for the particular zone. For example, the each index trace generated for the same zone, the controller 190 can fit a linear function to the index values of that index trace, and determine a goodness of fit of that linear function to the sequence of index values. The index trace generated having the line with the best goodness of fit its own index values can be selected as the index trace for the particular zone and substrate. For example, when determining how to adjust the polishing rates of the adjustable zones, e.g., at time T0, the linear function with the best goodness of fit can be used in the calculation. As another example, endpoint can be called when the calculated index (as calculated from the linear function fit to the sequence of index values) for the line with the best goodness of fit matches or exceeds the target index. Also, rather than calculating an index value from the linear function, the index values themselves could be compared to the target index to determine the endpoint.

Determining whether an index trace associated with a spectra library has the best goodness of fit to the linear function associated with the library can include determining whether the index trace of the associated spectra library has the least amount of difference from the associated robust line, relatively, as compared to the differences from the associated robust line and index trace associated with another library, e.g., the lowest standard deviation, the greatest correlation, or other measure of variance. In one implementation, the goodness of fit is determined by calculating a sum of squared differences between the index data points and the linear function; the library with the lowest sum of squared differences has the best fit.

Figure 13:
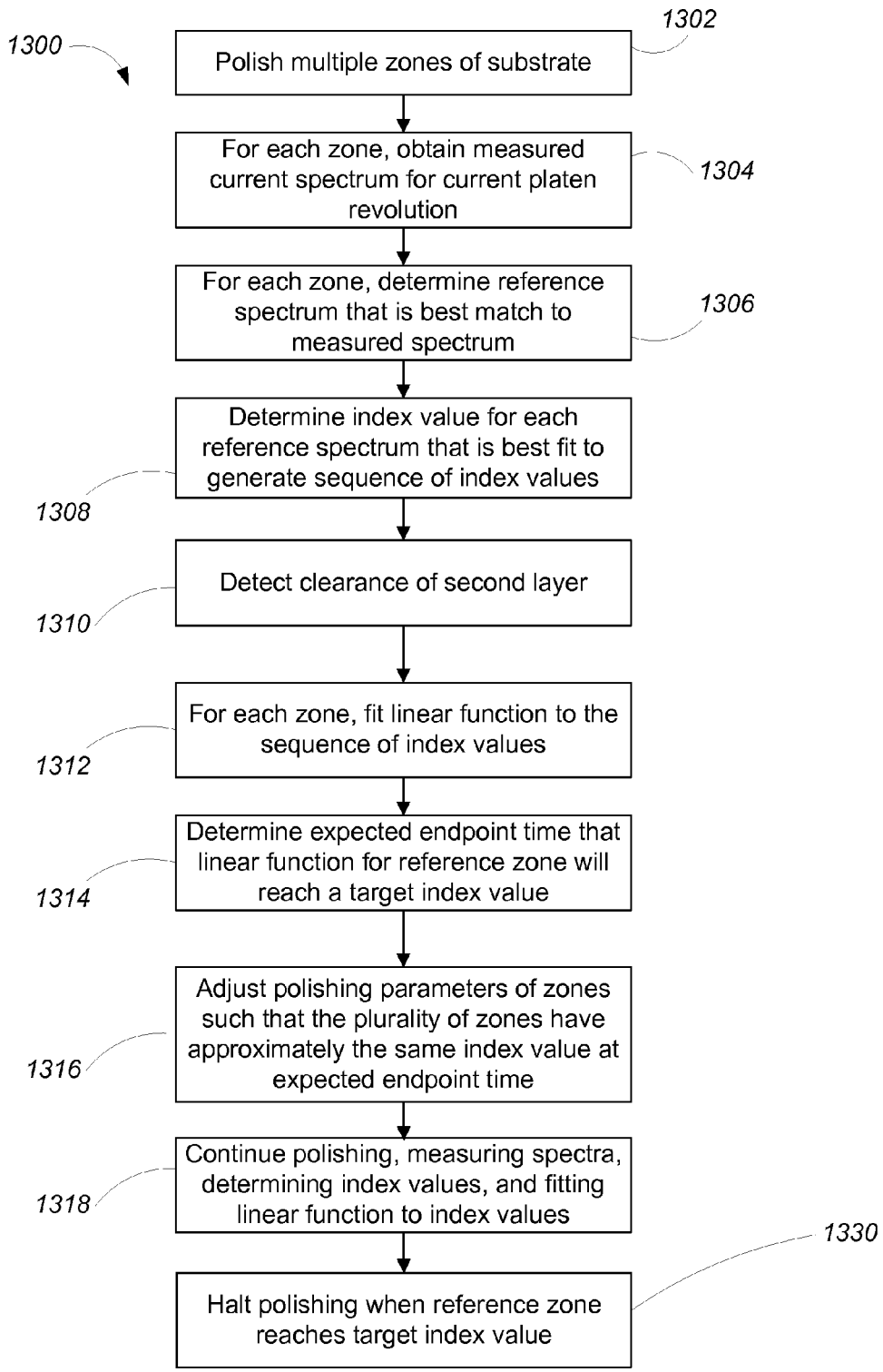
FIG. 13 is a flow diagram of an example process for adjusting the polishing rate of a plurality of zones in a plurality of substrates such that the plurality of zones have approximately the same thickness at the target time.

Referring to FIG. 13, a summary flow chart 1300 is illustrated. A plurality of zones of a substrate are polished in a polishing apparatus simultaneously with the same polishing pad (step 1302) as described above. During this polishing operation, each zone has its polishing rate controllable independently of the other substrates by an independently variable polishing parameter, e.g., the pressure applied by the chamber in carrier head above the particular zone. During the polishing operation, the substrate is monitored (step 1304) as described above, e.g., with a sequence of measure spectra obtained from each zone. For each measured spectrum in the sequence, the reference spectrum that is the best match is determined (step 1306). The index value for each reference spectrum that is the best fit is determined to generate sequence of index values (step 1308).

Clearance of the second layer is detected (step 1310). For each zone, a linear function is fit to the sequence of index values for spectra collected after clearance of the second layer is detected (step 1302). In one implementation, an expected endpoint time that the linear function for a reference zone will reach a target index value is determined, e.g., by linear interpolation of the linear function (step 1314). In other implementations, the expected endpoint time is predetermined or calculated as a combination of expected endpoint times of multiple zones. If needed, the polishing parameters for the other zones are adjusted to adjust the polishing rate of that substrate such that the plurality of zones reach the target thickness at approximately the same time or such that the plurality of zones have approximately the same thickness (or a target thickness) at the target time (step 1316). Polishing continues after the parameters are adjusted, and for each zone, measuring a spectrum, determining the best matching reference spectrum from a library, determining the index value for the best matching spectrum to generate a new sequence of index values for the time period after the polishing parameter has been adjusted, and fitting a linear function to index values (step 1318). Polishing can be halted once the index value for a reference zone (e.g., a calculated index value generated from the linear function fit to the new sequence of index values) reaches target index (step 1330).

In some implementations, the sequence of index values is used to adjust the polishing rate of one or more zones of a substrate, but another in-situ monitoring system or technique is used to detect the polishing endpoint.

Although the discussion above assumes a rotating platen with an optical endpoint monitor installed in the platen, system could be applicable to other types of relative motion between the monitoring system and the substrate. For example, in some implementations, e.g., orbital motion, the light source traverses different positions on the substrate, but does not cross the edge of the substrate. In such cases, the collected spectra can still be grouped, e.g., spectra can be collected at a certain frequency and spectra collected within a time period can be considered part of a group. The time period should be sufficiently long that five to twenty spectra are collected for each group.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., the substrate can be a bare wafer, or it can include one or more deposited and/or patterned layers. The term substrate can include circular disks and rectangular sheets.

Embodiments and all of the functional operations described in this specification can be implemented in digital electronic circuitry, or in computer software, firmware, or hardware, including the structural means disclosed in this specification and structural equivalents thereof, or in combinations of them. Embodiments can be implemented as one or more computer program products, i.e., one or more computer programs tangibly embodied in a machine-readable storage media, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs in one or more computer systems to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

The above described polishing apparatus and methods can be applied in a variety of polishing systems. Either the polishing pad, or the carrier heads, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation.

Particular embodiments of the invention have been described. Other embodiments are within the scope of the following claims.

What is claimed is:

1. A method of controlling polishing, comprising:
generating a library of reference spectra, comprising:
storing at least one reference spectrum;
storing a plurality of different transmission curves, the transmission curves representing distortion to a spectrum introduced by variations in components in an optical path before a substrate surface;
for at least two transmission curves from the plurality of different transmission curves, calculating a modified reference spectrum from the reference spectrum and the transmission curve to generate a plurality of modified reference spectra;
polishing a substrate;
measuring a sequence of spectra of light from the substrate during polishing;
for each measured spectrum of the sequence of spectra, finding a best matching reference spectrum from the plurality of modified reference spectra to generate a sequence of best matching reference spectra; and
determining at least one of a polishing endpoint or an adjustment for a polishing rate based on the sequence of best matching reference spectra.

2. The method of claim 1, wherein the different transmission curves represent variations in transmission of one or more windows.

3. The method of claim 2, wherein the different transmission curves represent distortion to a spectrum at different ages of a window of a polishing pad.

4. The method of claim 2, wherein different transmission curves represent different windows.

5. The method of claim 1, wherein the different transmission curves represent distortion to a spectrum at different ages of a bulb from a light source.

6. The method of claim 1, further comprising receiving user input identifying the at least two transmission curves from the plurality of different transmission curves.

7. The method of claim 1, further comprising generating the plurality of different transmission curves.

8. The method of claim 7, wherein generating the plurality of different transmission curves comprises calculating the transmission curves from an optical model.

9. The method of claim 1, wherein calculating the modified reference spectrum comprises multiplying the reference spectrum by the transmission curve.

10. The method of claim 9, wherein the transmission curve is stored as a ratio between 0 and 1 as a function of wavelength.

11. The method of claim 1, further comprising generating the at least one reference spectrum.

12. The method of claim 11, wherein generating the at least one reference spectrum comprises measuring a test substrate during a polishing operation using the an optical monitoring system that includes the optical path.

13. The method of claim 11, wherein generating the at least one reference spectrum comprises calculating the reference spectrum from an optical model.

14. A method of generating a library of reference spectra, comprising:
storing at least one reference spectrum;
storing a plurality of different transmission curves, the transmission curves representing distortion to a spectrum introduced by variations in components in an optical path before a substrate surface; and
for at least two transmission curves from the plurality of different transmission curves, calculating a modified reference spectrum from the reference spectrum and the transmission curve to generate a plurality of modified reference spectra;
wherein generating the plurality of different transmission curves comprises measuring a base spectrum from a test substrate using an in-situ optical monitoring system and measuring one or more additional spectra from the same test substrate or another test substrate of the same material using the in-situ optical monitoring system at different times, and calculating the transmission curves from the base spectrum and the one or more additional spectra.

15. The method of claim 14, wherein the different times are at different ag of a window of polishing pad in an optical path between the test substrate and a light source or detector of the in-situ optical monitoring system.

16. The method of claim 14, wherein the different times are at different ag of a bulb of a light source of the in-situ optical monitoring system.

17. The method of claim 14, wherein calculating the transmission curves comprises a division operation in which the additional spectrum is in the numerator and the bas spectrum is in the denominator.

18. The method of claim 14, further comprising measuring a first dark spectrum at the same age of the window as the base spectrum and measuring a second dark spectrum at the same age of the window as the additional spectrum.

19. The method of claim 18, wherein calculating the transmission curves comprises calculating $$T = \frac{A - D_A}{B - D_B}$$

where A is the additional spectrum, $D_A$ is the second dark spectrum, B is the base spectrum, and $D_B$ is the first dark spectrum.

20. The method of claim 14, wherein the test substrate comprises a bare silicon wafer.

* * * * *

UNITED STATES PATENT AND TRADEMARK OFFICE
CERTIFICATE OF CORRECTION

PATENT NO. : 8,547,538 B2
APPLICATION NO. : 13/091965
DATED : October 1, 2013
INVENTOR(S) : Jeffrey Drue David It is certified that error appears in the above-identified patent and that said Letters Patent is hereby corrected as shown below:

In the Claims:

In Claim 15, column 22, line 53, delete "ag" and insert -- ages --.

In Claim 16, column 22, line 58, delete "ag" and insert -- ages --.

In Claim 17, column 22, line 62, delete "bas" and insert -- base --.

Signed and Sealed this
Third Day of December, 2013

Margaret A. Focarino
*Commissioner for Patents of the United States Patent and Trademark Office*